(12) United States Patent
Schulingkamp et al.

(10) Patent No.: US 7,939,052 B2
(45) Date of Patent: May 10, 2011

(54) METHOD OF MEASURING THE BIOLOGICAL ACTIVITY OF AN UROTENSIN II RECEPTOR

(75) Inventors: Robert Schulingkamp, Warminster, PA (US); Jianshen Qi, Chalfont, PA (US); Raymond Colburn, Chalfont, PA (US); Dennis Stone, Telford, PA (US); Christopher Van Besien, Cambridge, MA (US); Lisa Minor, Flemington, NJ (US); Patricia Andrade-Gordon, Doylestown, PA (US); Bruce Damiano, Warrington, PA (US)

(73) Assignee: Janssen Pharmaceutica NV (BE)

( * ) Notice: Subject to any disclaimer, the term of this patent is extended or adjusted under 35 U.S.C. 154(b) by 326 days.

(21) Appl. No.: 11/432,465

(22) Filed: May 11, 2006

(65) Prior Publication Data
US 2006/0280686 A1    Dec. 14, 2006

Related U.S. Application Data

(60) Provisional application No. 60/680,449, filed on May 12, 2005.

(51) Int. Cl.
*A61K 49/00* (2006.01)
*A61K 38/17* (2006.01)
(52) U.S. Cl. ............... 424/9.2; 514/7; 514/12; 514/109
(58) Field of Classification Search ............. 424/9.2, 424/9.7; 514/7, 12, 109, 312, 350; 530/317
See application file for complete search history.

(56) References Cited

U.S. PATENT DOCUMENTS

| | | | |
|---|---|---|---|
| 5,223,409 A | | 6/1993 | Ladner et al. |
| 5,571,698 A | | 11/1996 | Ladner et al. |
| 2003/0216407 A1* | | 11/2003 | Butt et al. ............. 514/252.16 |
| 2004/0077529 A1* | | 4/2004 | Lehmann et al. ........... 514/7 |
| 2005/0075480 A1* | | 4/2005 | Coy et al. ............... 530/317 |

OTHER PUBLICATIONS

Sheila A Doggrell, Urotensin-II and the cardiovasuclar system—the importance of developing modulators, Expert. Opin. Investig. Drugs (2004, 13(5), 479-487.*
Jennifer L. Davison, Daniel S. Short and Thad E. Wilson, Effect of local heating and vasodilation on the cutaneous venoarteriolar response, Clin Auton res. (2004), 14, 385-390.*
Ames, et al., "Human Urotensin-II is a Potent Vasoconstrictor and Agonist for the Orphan Receptor GPR14", Nature, 1999, 401(6750), pp. 282-286.
Bottrill, et al., "Human Urotensin-II is an Endothelium-Dependent Vasodilator in Rat Small Arteries", British Journal of Pharmacology, 2000, 130(8), pp. 1865-1870.
Camarda, et al., "Urantide Mimics Urotensin-II Induced Calcium Release in Cells Expressing Recombinant UT Receptors", European Journal of Pharmacology, 2004, 498(1-3), pp. 83-86.

Conlon et al., "Distribution and Molecular Forms of Urotensin II and its Role in Cardiovascular Regulation in Vertebrates", The Journal of Experimental Zoology, 1996, 275, pp. 226-238.
Coulouarn et al., "Cloning of the cDNA Encoding the Urotensin II Precursor in Frog and Human Reveals Intense Expression of the Urotensin II Gene in Motoneurons of the Spinal Cord", Procedural National Academy of Science USA, 1998, 95, pp. 15803-15808.
Coulouarn et al., "Cloning, Sequence Analysis and Tissue Distribution of the Mouse and Rat Urotensin II Precursors", FEBS Letters, 1999, 457(1), pp. 28-32.
Cull et al., "Screening for Receptor Ligands Using Large Libraries of Peptides Linked to the C Terminus of the *lac* Repressor", Procedure National Academy of Sciences, USA, 1992, 89, pp. 1865-1869.
Douglas, et al., "Differential Vasoconstrictor Activity of Human Urotensin-II in Vascular Tissue Isolated from the Rat, Mouse, Dog, Pig, Marmoset and Cynomolgus Monkey", British Journal of Pharmacology, 2000, 131(7): 1262-74.
Douglas et al., "From 'Gills to Pills': Urotensin-II as a Regulator of Mammalian Cardiorenal Function", Trends in Pharmacological Sciences, 2004, 25(2), pp. 76-85.
Elshourbagy et al., "Molecular and Pharmacological Characterization of Genes Encoding Urotensin-II Peptides and Their Cognate G-Protein-Coupled Receptors from the Mouse and Monkey, British Journal of Pharmacology", 2002, 36, pp. 9-22.
Fodor et al., "Multiplexed Biochemical Assays with Biological Chips", Nature, 1993, 364, pp. 555-556.
Gardiner, et al., "Depressor and Regionally-Selective Vasodilator Effects of Human and Rat Urotensin II in Conscious Rates", British Journal of Pharmacology, 2001, 132(8), pp. 1625-1629.
Gardiner, et al., "Bolus Injection of Human UII in Conscious Rats Evokes a Biphasic Haemodynamic Response", British Journal of Pharmacology, 2004, 143(3), pp. 422-430.
Gray et al., "Human Urotensin II Increases Coronary Perfusion Pressure in the Isolated Rat Heart Potentiation by Nitric Oxide Synthase and Cyclooxygenase Inhibition", Life Sciences, 2001, 69(2), pp. 175-180.
Hassan, et al., "Effect of Human Urotensin-II Infusion on Hemodynamics and Cardiac Function[1,2]", Canadian Journal of Physiol. Pharmacology, 2003, 81(2), pp. 125-128.
Houghten, et al., "The Use of Synthetic Peptide Combinatorial Libraries for the Identification of Bioactive Peptides", Biotechniques, 1992, 13, pp. 412-421.
Katano, et al., "Vasodilator Effect of Urotensin II, One of the Most Potent Vasoconstricting Factors, on Rat Coronary Arteries", European Journal of Pharmacology, 2000, 402(1-2) pp. 209-211.
Lam, et al., "A New Type of Synthetic Peptide Library for Identifying Ligand-Binding Activity", Nature, 1991, 354, pp. 82-84.

(Continued)

*Primary Examiner* — Michael G Hartley
*Assistant Examiner* — Jagadishwar R Samala (57) ABSTRACT

Administration of U-II to rats caused an increase in the redness or the skin temperature of the ear of the rats. The increase was inhibited by compounds that decease the biological activity of the U-II/UT receptor. Thus, the present invention provides methods of measuring the biological activity of an U-II receptor by monitoring the redness or the skin temperature of the ear of an animal, and the use of the methods to test compounds for their abilities to increase or decrease the biological activity of an U-II receptor.

12 Claims, 8 Drawing Sheets

OTHER PUBLICATIONS

Lam, et al., "Application of Combinatorial Library Methods in Cancer Research and Drug Discovery", Anti-Cancer Drug Design, 1997, 12, pp. 145-167.

Lin et al., "Central Cardiovascular Action of Urotensin II in Conscious Rats", Journal of Hypertension, 2003, 21(1), pp. 159-165.

Maguire et al., "Orphan-Receptor Ligand Human Urotensin II:Receptor Localization in Human Tissues and Comparison of Vasoconstrictor Responses with Endothelin-1", British Journal of Pharmacology, 2000, 131(3), pp. 441-446.

Marchese, et al., Cloning and Chromosomal Mapping of Three Novel Genes, GPR9, GPR10, and GPR14, Encoding Receptors Related to Interleukin 8, Neuropeptide Y, and Somatostatin Receptors, Genomics, 1995, 29, pp. 335-344.

Ohsako, et al., "Cloning and Sequence Analysis of cDNAs Encoding Precursors of Urotensin II-a and -y", The Journal of Neuroscience, 1986, 6, pp. 2730-2735.

Patacchini, et al., "Urantide: an Ultrapotent Urotensin II Antagonist Peptide in the Rat Aorta", British Journal of Phrmacology, 2003, 140(7), pp. 1155-1158.

Russell, "Emerging Roles of Urotensin-II in Cardiovascular Disease", Pharmacology & Therapeutics, 2004, 103, pp. 223-243.

Scott, et al., "Searching for Peptide Ligands with an Epitope Library", Science, 1990, 249, pp. 386-390.

Sugo, et al., "Identification of Urotensin II-related Peptide as the Urotensin II-Immunoreactive Molecule in the Rat Brain", Biochemical and Biophysical Research Communications, 2003, 310, pp. 860-868.

Turenne, et al., An Animal Model of Nicotinic-Acid-Induced Vasodilation: Effect of Halpperidol, Caffeing and Nicotine Upon Nicotonic Acid Response, 2001, 50(3), pp. 191-197.

Zhang, et al., "Urotensin II is a Nitric Oxide-Dependent Vasodilator and Natriuretic Peptide in the Rat Kidney", American Journal of Physiology Renal Physiology, 2003, 285, F792-F798.

Zuckermann, et al., Discovery of Nanomolar Ligands for 7-Transmembrane G-Protein-Coupled Receptors from a Diverse N-(Substituted)Glycine Peptoid Library, Journal of Med. Chem., 1994, 37, pp. 2678-2685.

* cited by examiner

SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Cys Phe Trp Lys Tyr Cys
 1               5

<210> SEQ ID NO 2
<211> LENGTH: 11
<212> TYPE: PRT
<213> ORGANISM: Homo sapiens

<400> SEQUENCE: 2

Glu Thr Pro Asp Cys Phe Trp Lys Tyr Cys Val
 1               5                  10

<210> SEQ ID NO 3
<211> LENGTH: 13
<212> TYPE: PRT
<213> ORGANISM: Rana ridibunda

<400> SEQUENCE: 3

Ala Gly Asn Leu Ser Glu Cys Phe Trp Lys Tyr Cys Val
 1               5                  10

<210> SEQ ID NO 4
<211> LENGTH: 12
<212> TYPE: PRT
<213> ORGANISM: Oncorhynchus mykiss

<400> SEQUENCE: 4

Gly Gly Asn Ser Glu Cys Phe Trp Lys Tyr Cys Val
 1               5                  10

<210> SEQ ID NO 5
<211> LENGTH: 12
<212> TYPE: PRT
<213> ORGANISM: Cyprinus carpio

<400> SEQUENCE: 5

Gly Gly Gly Ala Glu Cys Phe Trp Lys Tyr Cys Val
 1               5                  10

<210> SEQ ID NO 6
<211> LENGTH: 12
<212> TYPE: PRT
<213> ORGANISM: Sus scrofa

<400> SEQUENCE: 6

Gly Thr Pro Ser Glu Cys Phe Trp Lys Tyr Cys Val
 1               5                  10

<210> SEQ ID NO 7
<211> LENGTH: 12
<212> TYPE: PRT
<213> ORGANISM: Sus scrofa

<400> SEQUENCE: 7

```
Gly Pro Pro Ser Glu Cys Phe Trp Lys Tyr Cys Val
  1               5                  10

<210> SEQ ID NO 8
<211> LENGTH: 13
<212> TYPE: PRT
<213> ORGANISM: Rattus norvegicus

<400> SEQUENCE: 8

His Gly Thr Ala Pro Glu Cys Phe Trp Lys Tyr Cys Ile
  1               5                  10

<210> SEQ ID NO 9
<211> LENGTH: 13
<212> TYPE: PRT
<213> ORGANISM: Mus musculus

<400> SEQUENCE: 9

His Gly Ala Ala Pro Glu Cys Phe Trp Lys Tyr Cys Ile
  1               5                  10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Cys Phe Trp Lys Tyr Cys Val
  1               5
```

METHOD OF MEASURING THE BIOLOGICAL ACTIVITY OF AN UROTENSIN II RECEPTOR

CROSS-REFERENCE TO RELATED APPLICATIONS

This application claims priority to Application No. 60/680,449 filed on May 12, 2005.

FIELD OF THE INVENTION

The present invention relates to methods of measuring the biological activities of an urotensin receptor. Particularly the present invention relates to methods of identifying compounds that increase or decrease the biological activities of an urotensin receptor by measuring the changes in the temperature or the redness of an ear of an animal.

BACKGROUND OF THE INVENTION

Urotensin-II (U-II) is a vasoactive, somatosatin-like cyclic peptide (Coulouarn et al., 1999, *FEBS Lett* 457(1): 28-32). U-II was originally isolated from the teleost urophysis, and was shown to be involved in the cardiovascular regulation, osmoregulation, and regulation of lipid metabolism in fish (Ohsaka et al., 1986, *J. Neurosci* 6:2730-2735; and Conlon et al., 1996, *J. Exp. Zool.* 275:226-238). The genes encoding orthologs of U-II precursor proteins have since been cloned from various species, for example, rat (Marchese et al., 1995, *Genomics* 29: 335-344), human (Coulouarn et al., 1998, *Proc. Natl. Acad. Sci. USA* 95: 15803-15808; and Ames et al., 1999, *Nature* 401(6750): 282-6), and mouse (Coulouarn et al., 1999, supra). Human U-II is found within both vascular and cardiac tissue (including coronary atheroma). In addition, U-II immunoreactivity is also found within central nervous system and endocrine tissues (Ames et al., supra).

G-protein-coupled receptor 14 (GPR14), also known as sensory epithelium neuropeptide-like receptor (SENR), was recently identified as to function as an U-II receptor (Ames et al., supra). GPR14 was cloned as an orphan receptor with similarity to members of the somatostatin/opioid family. Human U-II binds to recombinant human GPR14 with high affinity and the binding is functionally coupled to calcium mobilization. The receptor of U-II (UT receptor) has also been identified and characterized from other animals, for example, mouse and monkey (Elshourbagy et al., 2002, *Br. J. Pharmacol.* 36: 9-22). The UT receptor is expressed abundantly in the spinal cord, and also in heart, lungs, blood vessels, kidney, and brain (Russell, 2004, *Pharmcology & Therapeutics* 103: 223-243).

Studies have demonstrated that U-II is both an endothelium independent vasoconstrictor (Ames et al., supra; Maguire et al., 2000, *Br. J. Pharmacol.* 131(3): 441-6] and an endothelium dependent vasodilator (Bottrill, 2000; *Br. J. Pharmacol.* 130(8): 1865-70; Zhang et al., 2003, *Am. J. Physiol. Renal. Physiol.*, 285, F792-8). The vasomotor profile of U-II exhibits significant species differences, as well as regional and functional differences between vessels (Douglas et al., 2000, *Br. J. Pharmacol.* 131(7): 1262-74). At higher concentrations, U-II induced a sustained vasodilation that was significantly inhibited by a cyclooxygenase inhibitor (Katano et al., 2000, *Eur. J. Pharmacol.* 402(1-2): R5-7). When directly administered into the renal artery, U-II increased renal blood flow as well as diuresis and naturesis in a dose-dependent manner, suggesting that U-II may produce renal vasodilation. These effects were abolished by L-NAME (Zhang et al., supra), the nitric oxide inhibitor. L-NAME increases the vasocontractile response of U-II (Maguire et al., supra). In isolated perfused rat heart, U-II elicited a concentration-dependent increase in coronary resistance (Gray et al., 2001, *Life Sciences* 69(2): 175-180). In the presence of L-NAME and the cyclooxygenase inhibitor, indomethacin, U-II significantly increased the coronary perfusion pressure three-fold, suggesting that U-II mediates the release of the vasodilators, nitric oxide and prostacyclin (Gray et al., supra).

Emerging roles of U-II in cardiovascular diseases have been implicated (Russell k supra). Recent evidence suggests that the UT receptor system is up-regulated in multi-organ disease states, such as congestive heart failure (CHF), pulmonary hypertension, and chronic renal failure. A number of non-peptide UT receptor antagonists have been developed with the aim of dampening harmful effects of over-activated UT receptors (see, i.e., Douglas et al, 2004, *Trends. Pharmacol. Sci.* 25: 76-85).

To facilitate the development of new compounds that regulate the biological activity of the UT receptor, there is a need to develop methods that allow simple measurement of the ability of a candidate compound to increase or decrease the biological activity of UT receptor.

SUMMARY OF THE INVENTION

It is now discovered that systemic administration of U-II in both conscious and anesthetized rats caused an increase in the redness and skin temperature of the ear of the rats. These effects were inhibited by compounds that decease the biological activity of the U-II/UT receptor system.

Thus, one general aspect of the invention is a method of monitoring the biological activity of an urotensin II receptor in an animal, comprising the step of measuring the redness or the skin temperature of an ear of the animal.

Another general aspect of the invention is a method of testing a candidate compound for its ability to increase the biological activity of an urotensin II receptor in an animal, comprising the steps of: (1) administering the candidate compound to the animal; (2) measuring the redness or the skin temperature of an ear of the animal within an effective time period; and (3) correlating an increase in the redness or the skin temperature of the ear of the animal with the ability of the candidate compound to increase the biological activity of the urotensin II receptor in the animal.

Yet, another general aspect of the invention is a method of testing a candidate compound for its ability to decrease the biological activity of an urotensin II receptor in an animal, comprising the steps of: (1) administering to the animal an effective amount of an agent that is known to increase the biological activity of an urotensin II receptor, wherein the effective amount of said agent induces an increase in the redness or the skin temperature of an ear of the animal within an effective time period; (2) administering to the animal the candidate compound; (3) measuring the redness or the skin temperature of an ear of the animal within the effective time period; and (4) correlating an inhibition of the agent-induced increase in the redness or the skin temperature of the ear of the animal with the ability of the candidate compound to decrease the biological activity of the urotensin II receptor in the animal.

In preferred embodiments, the animal used in the methods of the invention is a rat.

BRIEF DESCRIPTION OF THE DRAWINGS

injected with vehicle (saline) or 10 µg/kg rat U-II. Significant increase in the redness of the ear was observed at about 15 min. after U-II administration, and lasted for about 30 min. Panel A and B are vehicle treated animals with B being a close up view of the rat, Panels C and D are U-II treated animals with Panel D being the close up view. All pictures were taken 20 minutes following either vehicle or U-II administration.

FIG. 2 is the time course of U-II induced increase in skin temperature of the rat ear. U-II, at various concentrations, was administrated via s.c to conscious rats in the doses indicated. The lateral ear surface temperature was measured before and after administration of U-II. The temperature change=the measured temperature at the time indicated—the measured temperature before U-II or vehicle administration. Each curve represents the average of 6 animals ±the S.E.M. Vehicle—filled square; U-II (0.3 µg/kg)—filled right side up triangle; U-II (0.9 µg/kg)—filled upside down triangle; U-II (3 µg/kg)—filled diamond; U-II (9 µg/kg)—filled circle; U-II (30 µg/kg)—open square; U-II (90 µg/kg)—asterisks; U-II (300 µg/kg)—open upside down triangle; U-II (667 µg/kg)—open diamond; U-II (2000 µg/kg)—open circle.

DETAILED DESCRIPTION OF THE INVENTION

All publications cited hereinafter are hereby incorporated by reference. Unless defined otherwise, all technical and scientific terms used herein have the same meaning as commonly understood to one of ordinary skill in the art to which this invention pertains.

It must be noted that as used herein and in the appended claims, the singular forms "a," "an," and "the" include plural reference unless the context clearly dictates otherwise. Thus, for example, a reference to "a cell" is a reference to one or more cells and includes equivalents thereof known to those skilled in the art and so forth.

As used herein, the terms "comprising", "containing", "having" and "including" are used in their open, non-limiting sense.

The following are some abbreviations that are at times used in this specification:
GPCR=G protein coupled receptor;
U-II=Urotensin-II;
URP=Urotensin-II-related peptide
L-NAME=$N^g$ nitro-L-arginine methylester;
UT=Urotensin-II receptor;
i.p.=intraplantar
s.c.=subcutaneous
i.v.=intravenous As used herein, "urotensin-II", "U-II", or "U2", used interchangeably herein, each refers to a peptide having a conserved cyclic hexapeptide, SEQ ID NO: 1, CFWKYC, wherein an intramolecular disulfide bond is formed between the two cysteines of the hexapeptide. Examples of "urotensin-II" include, but are not limited to, those listed in Table 1, with an intramolecular disulfide bond between two the cysteines of the hexapeptide as listed in SEQ ID NO: 1. "Urotensin-II" also includes the so-called U-II-related peptide (URP), for example, consisting essentially of SEQ ID NO: 10, ACF-WKYCV, with an intramolecular disulfide bond formed between the two cysteines (Sugo et al., 2003, *Biochem Biophys Res Commun* 2003; 310:860-8). An "urotensin-II" can be isolated from a natural source, such as an U-II producing animal. An "urotensin-II" can also be synthesized via any in vitro method, such as an in vitro peptide synthesis reaction.

TABLE 1

Examples of urotensin-II from various species

| Species | Sequence of urotensin-II |
|---|---|
| Human | SEQ ID NO: 2, ETPDCFWKYCV |
| Frog | SEQ ID NO: 3, AGNLSECFWKYCV |
| Trout | SEQ ID NO: 4, GGNSECFWKYCV |
| Carp α | SEQ ID NO: 5, GGGAECFWKYCV |
| Porcine-1 | SEQ ID NO: 6, GTPSECFWKYCV |
| Porcine-2 | SEQ ID NO: 7, GPPSECFWKYCV |
| Rat-1 | SEQ ID NO: 8, HGTAPECFWKYCI |
| Mouse | SEQ ID NO: 9, HGAAPECFWKYCI |

A "functional derivative of urotensin-II" is a chemical entity that is derived from an urotensin-II, which still has all or part of the biological activity of urotensin-II, i.e., to bind to an urotensin-II receptor, and the binding can be functionally coupled to calcium mobilization. Examples of functional derivative of urotensin-II include, but are not limited to, modifications or truncations of urotensin-II, or fusion proteins comprising urotensin-II, that maintain all or part of the biological activities of an urotensin-II.

A "functional equivalent of urotensin-II" is a chemical entity that has all or part of the biological activity of urotensin-II, i.e., to bind to an urotensin-II receptor, and the binding can be functionally coupled to calcium mobilization. "Functional equivalent of urotensin-II" include "functional derivative of urotensin-II". "Functional equivalent of urotensin-II" also include, but are not limited to, the non-peptide U-II mimetics, non-peptide UT receptor agonists, inverse agonists and antagonists.

As used herein, an "urotensin II receptor", "U-II receptor", "UTR2", "UT receptor" or "U2R", used interchangeably herein, each refers to a G-protein-coupled receptor protein that binds to an urotensin II (U-II) or an analog thereof, and the binding can be functionally coupled to calcium mobilization. An "urotensin II receptor", can (1) have greater than about 60% amino acid sequence identity to a human U-II receptor (NCBI protein accession number: NP_061822); (2) bind to antibodies, e.g., polyclonal or monoclonal antibodies, raised against a human U-II receptor (NCBI protein accession number: NP_061822); or (3) be encoded by a polynucleotide that specifically hybridizes under stringent hybridization conditions to a nucleic acid molecule having a sequence that has greater than about 60% nucleotide sequence identity to the coding region of a human U-II receptor cDNA (NCBI nucleotide accession number: NM_018949).

"Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprising hybridization in 6× sodium chloride/sodium citrate (SSC) at about 45° C., followed by one or more washes in 0.2×SSC and 0.1% SDS at 50-65° C.

In some embodiments, the "U-II receptor" has greater than about 65, 70, 75, 80, 85, 90, or 95 percent amino acid sequence identity to a human U-II receptor (NCBI protein accession number: NP-061822). Exemplary U-II receptor includes human U-II receptor, which includes structural and functional polymorphisms of the human U-II receptor depicted in NCBI protein accession number: NP_061822. "Polymorphism" refers to a set of genetic variants at a particular genetic locus among individuals in a population. U-II receptor also includes orthologs of the human U-II receptor in other animals such as rat (i.e., NCBI protein accession NO: NP_065412), mouse (i.e., NCBI protein accession NO: NP_663415), pig, dog and monkey.

As used herein, "a biological activity of an urotensin II receptor" refers to an activity exerted by the urotensin II receptor as determined in vivo, or in vitro, according to standard techniques. Such an activity can be a direct activity such as the ability of an urotensin II receptor to bind to an urotensin II (U-II) or an analog thereof, and the binding can be functionally coupled to calcium mobilization. A biological activity of an urotensin II receptor can also be an indirect activity, such as a signal transduction activity mediated by the urotensin II receptor via its interaction with one or more than one additional protein or other molecule(s), including but not limited to, interactions that occur in a multi-step, serial fashion. For example, an urotensin II receptor has the biological activity of mediating the function of U-II or a functional derivative thereof as an endothelium independent vasoconstrictor or an endothelium dependent vasodilator.

A "signal transduction" is the cascade of processes by which an extracellular signal interacts with a receptor at a cell surface, causing a change in the level of a second messenger, and ultimately effects a change in the cell function.

A "signal transduction activity mediated by urotensin II receptor" refers to a signal transduction, wherein the extracellular signal is urotensin II or a functional equivalent thereof. In one embodiment, a "signal transduction activity mediated by urotensin II receptor" is the cascade of processes by which urotensin II binds to an urotensin II receptor at a cell surface, causing a change in the level of a second messenger, such as calcium or cyclic AMP, and ultimately effects a change in the cell's function. The change in the cell's function can be the change of any cellular process urotensin II is involved in. Changes in the cell's function often lead to changes of the animal physiology. For example, a "signal transduction activity mediated by urotensin II receptor" can be an endothelium independent vasoconstriction or an endothelium dependent vasodilation triggered by urotensin II.

As described herein, a "test molecule", "test compound", or "candidate compound", used interchangeably herein, each means a molecule that is subjected to the assay systems and methods described herein. Test compounds or candidate compounds encompass numerous chemical classes, although typically they are organic compounds. Preferably, they are small organic compounds, i.e., those having a molecular weight of more than 50 yet less than about 2500. Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of chloride channel activity. Therefore, a source of candidate agents is libraries of molecules based on a known compound that increases or decreases the biological activity of a U-II receptor, in which the structure of the known compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries.

A variety of other reagents also can be included in the method. These include reagents such as salts, buffers, neutral proteins (e.g., albumin), detergents, etc. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J. Med. Chem.* 37:2678. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,571,698), plasmids (Cull et al. (1992) *Proc. Natl. Acad. Sci. USA* 89:1865-1869) or phage (see e.g., Scott and Smith (1990) *Science* 249:3 86-390).

The present invention provides in vivo methods for identifying compounds that increase or decrease the biological activity of an U-II receptor. The inventive assay methods can be used to detect test compounds that increase or decrease the biological activity of an U-II receptor in any manner. Compounds that increase or decrease the biological activity of an U-II receptor can be compounds that interact directly with the U-II receptor in such a way as to affect the biological activity of U-II receptor. For example, such a compound can bind to the U-II receptor and affect the interaction of the receptor with U-II or other protein/molecule, such as a functional derivative of U-II, e.g., an U-II mimetic, or an agonist or antagonist of the U-II. Compounds that increase or decrease the biological activity of an U-II receptor can also be compounds that interact indirectly with the U-II receptor in such a way as to affect the biological activity of U-II receptor. Such a compound can bind to protein(s) or molecules other than the U-II receptor, and affect the signal transduction activity of the U-II receptor. For example, such as a compound can increase or decrease the amount or activity of a factor from the vascular endothelium, e.g., nitric oxide or prostacyclin, that is involved in the U-II receptor mediated vasodilation.

One general aspect of the invention is a method of monitoring the biological activity of an urotensin II receptor in an animal, comprising the step of measuring the redness or the skin temperature of an ear of the animal.

Another general aspect of the invention is a method of testing a candidate compound for its ability to increase the biological activity of an urotensin II receptor in an animal, comprising the steps of: (1) administering the candidate compound to the animal; (2) measuring the redness or the skin temperature of an ear of the animal within an effective time period; and (3) correlating an increase in the redness or the skin temperature of the ear of the animal with the ability of the candidate compound to increase the biological activity of the urotensin II receptor in the animal.

Yet, another general aspect of the invention is a method of testing a candidate compound for its ability to decrease the biological activity of an urotensin II receptor in an animal, comprising the steps of: (1) administering to the animal an effective amount of an agent that is known to increase the biological activity of an urotensin II receptor, wherein the effective amount of said agent induces an increase in the redness or the skin temperature of an ear of the animal within an effective time period; (2) administering to the animal the candidate compound; (3) measuring the redness or the skin temperature of an ear of the animal within the effective time period; and (4) correlating an inhibition of the agent-induced increase in the redness or the skin temperature of the ear of the animal with the ability of the candidate compound to decrease the biological activity of the urotensin II receptor in the animal.

A variety of animal species can be used in the method of the invention. For example, as illustrated in the Examples, rats can be used. Other animals that can be used include, but are not limited to, rabbits, hamster, guinea pigs, etc.

Compounds can be administered to an animal by any conventional route of administration, including, but not limited to, intravenous, oral, subcutaneous, intramuscular, intradermal and parenteral. Depending on the route of administration, compounds can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

The term "effective time period" as used herein, means the duration of time following the administration of a compound to an animal, with which a compound-induced changes in the redness or the skin temperature of an ear of the animal can be measured. The "effective time period", can vary depending upon the particular compound used, the mode of administration, and the strength of the preparation. In addition, factors associated with the particular animal being tested, including animal age, weight, diet and time of administration, can also result in changes of the "effective time period". Methods are known in the art for determining the range of "effective time period" for a testing animal. For example, a skilled artisan can determine the range of "effective time period" experimentally by testing known active compounds at various dosages with a particular route of compound administration, and measuring the redness or skin temperature of the ear of the animal at various time points after administration of the active compounds.

In some embodiments, when a rat is used as the testing animal, the "effective time period" can be 0-6 h, 0-5 h, 0-4 h, 0-3 h, 0-2 h, 0-1 h, or 15-40 min after the administration of the compound.

In the method of identifying a compound that decreases the biological activity of the U-II receptor, compounds that are known to activate or increase the biological activity of an U-II receptor can be administered to the animal to induce an increase in the redness or the skin temperature of an ear of the animal. For example, U-II or functional derivatives of U-II can be used for this purpose.

The term "effective amount of an agent" as used in this aspect, means that amount of an active compound that elicits an increase in the redness or the skin temperature of an ear of the animal when the active compound is administered to the animal. The effective amount may be varied depending upon the particular compound used, the mode of administration, and the strength of the preparation. In addition, factors associated with the particular animal being tested, including animal age, weight, diet and time of administration, will result in the need to adjust dosages. Methods are known in the art for determining the "effective amount of an agent". For example, a skilled artisan can determine the effective amount empirically by varying the amount of active compound used and measuring the redness or skin temperature of the ear of the animal after the administration of the compound.

In some embodiments, when U-II is used to induce an increase in the redness or the skin temperature of an ear of rat, the "effective amount of an U-II" can be 0.1 µg to 10 mg, 0.3 µg/kg to 3 mg/kg, 1 µg/kg to 1 mg/kg, 10 µg/kg to 500 µg/kg, or 50 µg/kg to 300 µg/kg.

In the method of identifying a compound that decreases the biological activity of the U-II receptor, agents that are known to activate or increase the biological activity of an U-II receptor can be administered to the animal prior to, concurrent with, or after the administration of the test compound to the animal.

Figure 1:
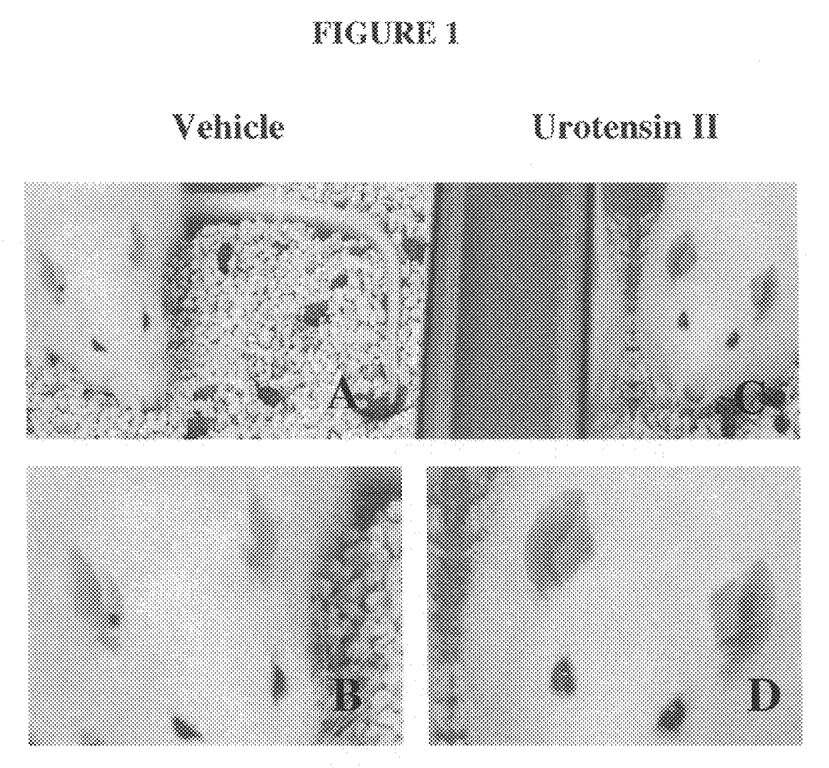
FIG. 1 illustrates the increased redness of the rat ear after administration of U-II. Rats were subcutaneously (s.c.)

The redness or skin temperature of the ear of the animal can be measured by various means known to a person skilled in the art. For example, the redness of the ear can be simply observed and evaluated by eyes, see for example FIG. 1. The skin temperature of the ear can be measured by any type of thermometer suitable for measuring skin temperature. For example, the skin temperature of the ear can be measured by a clinical thermometer, a single-detector radiation thermometer, or an infra-red thermometer, etc. Depending on the animal being used in the assay, one means of measurement may be preferred over another. An animal that is less sensitive to the administration of U-II would require a more sensitive means of measurement.

In an illustrative embodiment, when a compound is tested for its ability to increase the U-II receptor biological activity, the redness or skin temperature of the ear of the animal can be measured prior to the administration of the compound to the animal to establish a base line or control of the redness or skin temperature of the ear. After administrating the test compound to the animal, the redness or skin temperature of the ear can be measured once or more than once at various time points within the effective time period. The increase in the redness or the skin temperature of the ear of the animal can be determined, for example, by comparing the redness or the skin temperature of the ear after the administration of the test compound with that of the base line or control. A compound that is capable of increasing the biological activity of an U-II receptor will induce an increase in the redness or skin temperature of the ear.

In another illustrative embodiment when a compound is tested for its ability to decrease the U-II receptor biological activity, the redness or skin temperature of the ear of the animal can be measured prior to the administration of any compound to the animal to establish a base line or control of the redness or skin temperature of the ear. The animal is administered with a test compound and an effective amount of an agent that is known to increase the biological activity of a U-II receptor and induce an increase in the redness or skin temperature of the ear of the animal. The test compound and the agent can be co-administered or administered at different time points. When the test compound is administered after the active agent, the test compound is administered within an effective time period when the agent-induced increase in the redness or the skin temperature of an ear of the animal can be measured. The redness or skin temperature of the ear of the animal can be measured once or more than once at various time points within the effective time period after the administration of the test compound. A compound that is capable of decreasing the biological activity of an U-II receptor will inhibit the agent-induced increase in the redness or the skin temperature of the ear of the animal.

As used herein, the phrase "an inhibition of the agent-induced increase in the redness or the skin temperature of the ear of the animal" means prevention, blocking, prohibiting, decreasing, lowering, or abolishing of the agent-induced increase in the redness or the skin temperature of the ear of the animal. Such an inhibition can be determined, for example, by comparing the redness or the skin temperature of the ear after the administration of the test compound with that from the animal that is administered with the active agent alone, not the test compound.

The methods of the invention can be combined with other means of testing a compound for its ability to increase or decrease the U-II biological activity. For example, compounds that increase or decrease the U-II biological activity can be first identified by their ability to bind to an U-II receptor and/or alter the U-II mediate calcium mobilization, then tested for their ability to alter the redness or the skin color of the ear of an animal. Compounds can also be tested by their ability to cause animal physiology changes other than ear temperature. For example, it was observed that systemic administration of human U-II to anethetized monkeys resulted in a decrease in total peripheral conductance and cardiac contractility (Ames, 1999, supra); intravenous bolus injection of U-II into anethetized rats produced a decrease in mean arterial pressure, left ventricular systolic pressure and cardiac contractility (Hassan, 2003, *Can J Physiol Pharmacol* 81(2): 125-8); bolus injection of U-II to conscious rats evokes an initial response consisting of tachycardia and hypotension, followed by a later phase (30-120 min post injection) of tachycardia and hypertension (Gardiner, 2004, *Br J Pharmacol* 143(3): 422-30); and indomethacin and L-NAME together prevented both phases of the haemodynamic responses to U-II (Gardiner, 2004, supra); in conscious rats the predominant hemodynamic effect of U-II is systemic vasodilatation with dose-dependent tachycardia (Gardiner, 2001 et al., *Br. J. Pharmacol.* 132(8): 1625-9; and Lin et al., 2003, *J. Hypertens* 21(1): 159-65).

This invention will be better understood by reference to the examples that follow. Those skilled in the art will readily appreciate that these examples are only illustrative of the invention and not limiting.

EXAMPLE 1

U-II Induced an Increase in the Redness or Skin Temperature of the Rat Ear

The examples described herein used conscious rat as the testing animal, although similar results were also observed from anesthetized rats. Other animals can also be utilized following similar procedures. All procedures involving animals were conducted in an animal facility fully accredited by the American Association for Assessment and Accreditation of Laboratory Animal Care (AAALAC) and in accordance with The Guide for the Care and Use of Laboratory Animals (NIH). Protocols were approved by the Internal Animal Care and Use Committee (IACUC). Results are expressed as mean±s.e. mean. Comparisons between groups were assessed using two-sided Student's t-test. $P<0.05$ was considered significant.

Unless otherwise indicated, Rat U-II was obtained from SIGMA (U-7507, St Louis, Mo.). Urantide was purchased from Peptide International (PUT-3639-P1, Louisville, Ky.). Experiments were performed with male, Sprague-Dawley rats (Charles River, Wilmington, Mass.), weighing 250-350 g.

Rats were acclimated at 18° C. for at least 1 hour before U-II administration. The room temperature was kept at 18° C. throughout ear surface temperature measurements. Rat U-II suspended in sterile saline (0.1 ml) at various concentrations was administered to a conscious rat via unilateral intraplantar (i.p.) injection over a period of 5 second. In the serial dose experiment, serial doses of U-II were administered to a conscious rat via subcutaneous (s.c.) routes. The lateral inner ear surface temperature of the rat was measured using a Raytek High Performance Infra-red Thermometer (Raytek Corp., Santa Cruz, Calif.) at different time points.

Figure 2:
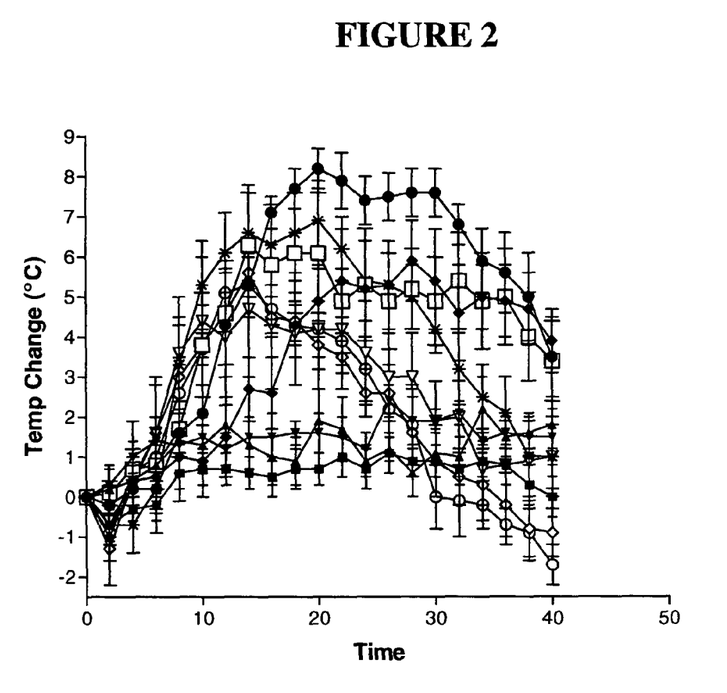

It was observed that following administration of U-II to a rat, the ears of the rat became red (FIG. 1) with a concomitant increase in the lateral ear surface temperature (FIG. 2). The ears of a rat are flat, with the blood vessels lying in a single plane. It has been reported that administration of nicotinic acid to a rat induces an increase of the ear temperature of less than about 1.5° C. (Turenne, 2001, *Schizophr Res* 50(3): 191-7). Distinguished from nicotinic acid, which has not been reported to affect the biological activity of U-II receptor, U-II induced a much greater increase in the ear temperature when it was administered to a rat, for example, up to 9° C. (FIG. 2). The increase in the redness and skin temperature of the ear was observed when U-II was administered to the rat via various means, such as via subcutaneous injection (FIG. 1), intramuscular injection (data not shown), and intravenous injection (data not shown).

Figure 3:
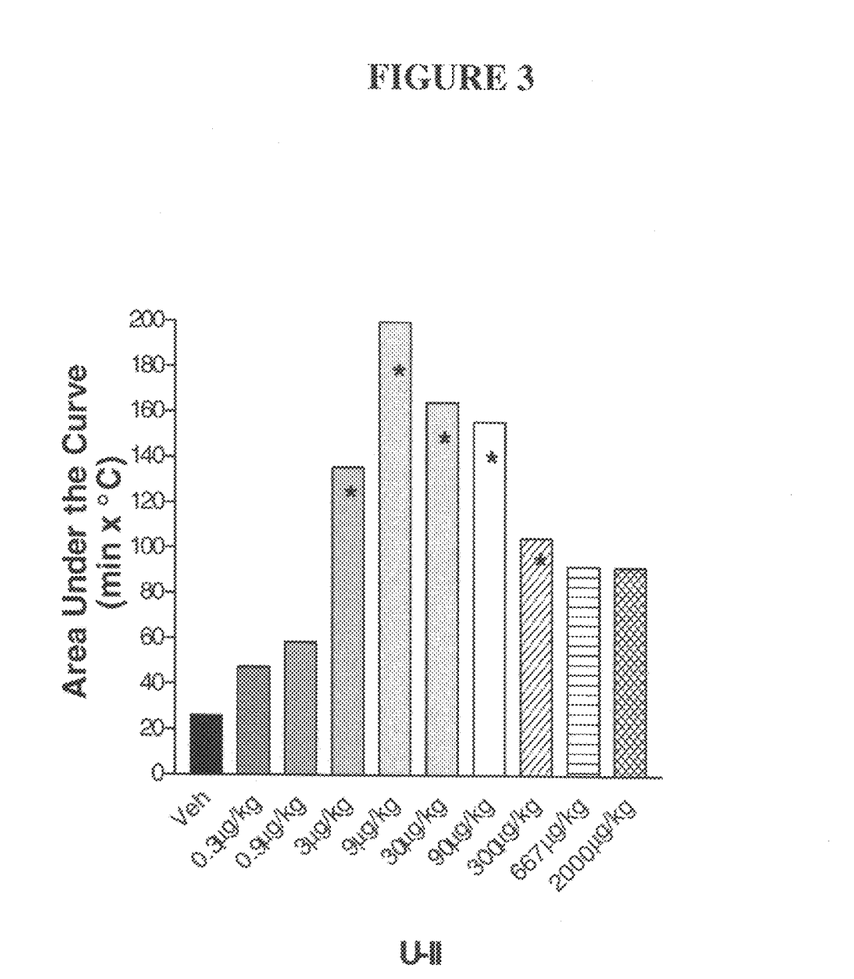
FIG. 3 illustrates the dose response of U-II induced increase in skin temperature of the rat. The data from experiments shown in FIG. 2 were calculated and plotted as area under the curve using Prism Software.

FIG. 2 illustrates the time course of the change in the skin temperature of the ear following subcutaneously administration of serial doses of U-II to the rat. The time course exhibited a bell shaped curve with the maximum effect achieved at about 15 to 30 min. after the administration of U-II to the rat. A dose of 9 µg/kg of U-II (FIG. 2 and FIG. 3) elicited the strongest increase in the skin temperature as compared to other lower or higher doses. The higher doses of U-II tended to induce an early peak response as compared to the lower doses of U-II.

Figure 4:
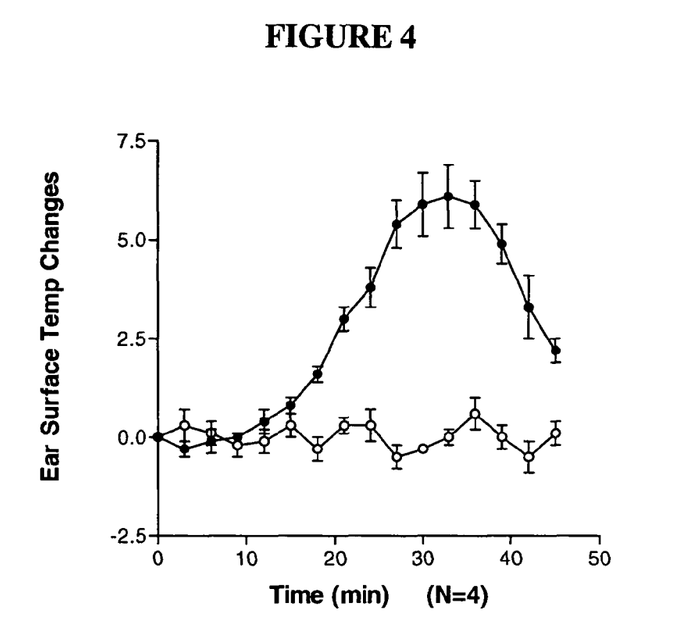
FIG. 4 illustrates that URP also induced an increase in skin temperature of the rat: URP at 100 µg/kg (filled circle), and vehicle (open circle). Each curve represents the average of 4 animals±the S.E.M.

Similarly, subcutaneous administration of URP (PUT-4408-V, Peptide International) also induced an increase in the redness or skin temperature of the rat (FIG. 4).

It was further observed that administration of U-II to an unconscious rat also induced an increase of the redness or skin temperature of the ear of the rat.

To explore the possibility that U-II induced increase in ear redness or skin temperature, i.e., ear flush, is related to thermoregulation, the core temperature was determined after U-II administration. Core temperature was measured rectally using a Kent Scientific (Torrington, Conn.) BAT-10 T type thermocouple multi-input thermometer. Rectal Probe used was a Kent Scientific (Style G) RET-2 Rectal probe for rats. Smooth ball tip with a stainless steel shaft −1" long, 0.59" dia., tip dia. 0.125", 5 ft. lead. Time constant 0.8 secs. The probe was coated with a water-based lubricant, inserted 1" into the rectum and secured to the base of the tail with adhesive tape. The rats were acclimated to this procedure for 1 hour daily, 5 days prior to the actual experiment. On the day of the experiment the probe was inserted and core temperature monitored until it stabilized. A baseline ear surface temperature was recorded and then U-II injected as described above.

Figure 5:
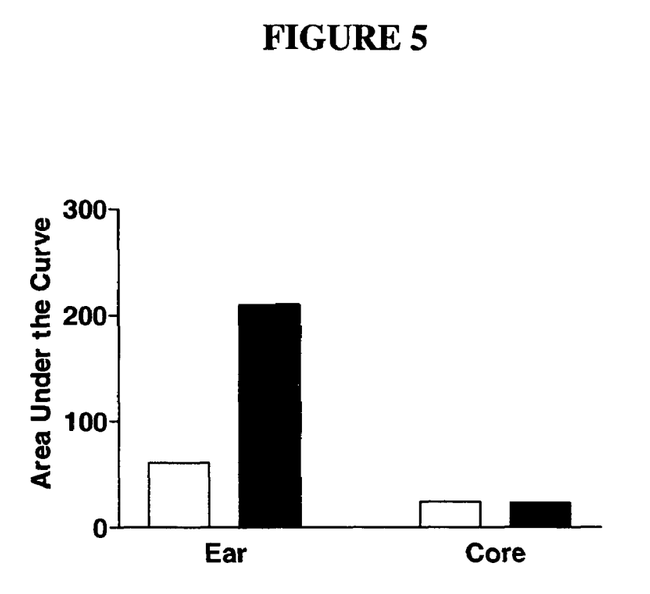
FIG. 5 is a comparison of the rat ear skin temperature and core temperature 40 minutes after U-II administration (140 µg/kg, s.c.) represented by area under the curve. Each bar represents the average of 6 animals. Vehicle—open bar; U-II (140 µg/kg)—filled bar.

No significant core temperature change was observed even when U-II was administrated at 140 µg/kg while significant ear flushing occurred (FIG. 5), suggesting that the U-II induced increase in the redness or skin temperature of the ear does not appear to be caused by thermal stress in the body.

EXAMPLE 2

Urantide Blocked U-II Induced Increase in the Redness or Skin Temperature of the Rat Ear A U-II antagonist peptide named urantide was recently discovered as a competitive, potent (pA2=8.3) and pure UT receptor antagonist in rat aorta vasoconstriction assays (Patacchini, 2003, *Br. J. Pharmacol.* 140(7): 1155-8). Utantide had minimal binding activity to proteins within a panel of receptor/ion channels (data not shown). A more recent report showed that urantide is a potent U-II agonist in CHO cells over-expressing the human UT receptor (Camarda, 2004, *Eur. J. Pharmacol.* 498(1-3): 83-6). This example tested the effect of urantide on the U-II induced increase in the redness or skin temperature of the rat ear. Other U-II antagonists or inverse agonist can be tested using similar protocols.

Urantide (PUT-3639-P1, Peptide International) was administered or co-administered with U-II (3 µg/kg) to a rat via subcutaneous administration. The lateral inner ear surface temperature of the rat was measured using a Raytek High Performance Infra-red Thermometer at different time points, wherein the time point of Urantide administration or Urantide and U-II co-administration was marked as 0 minute.

Figure 6:
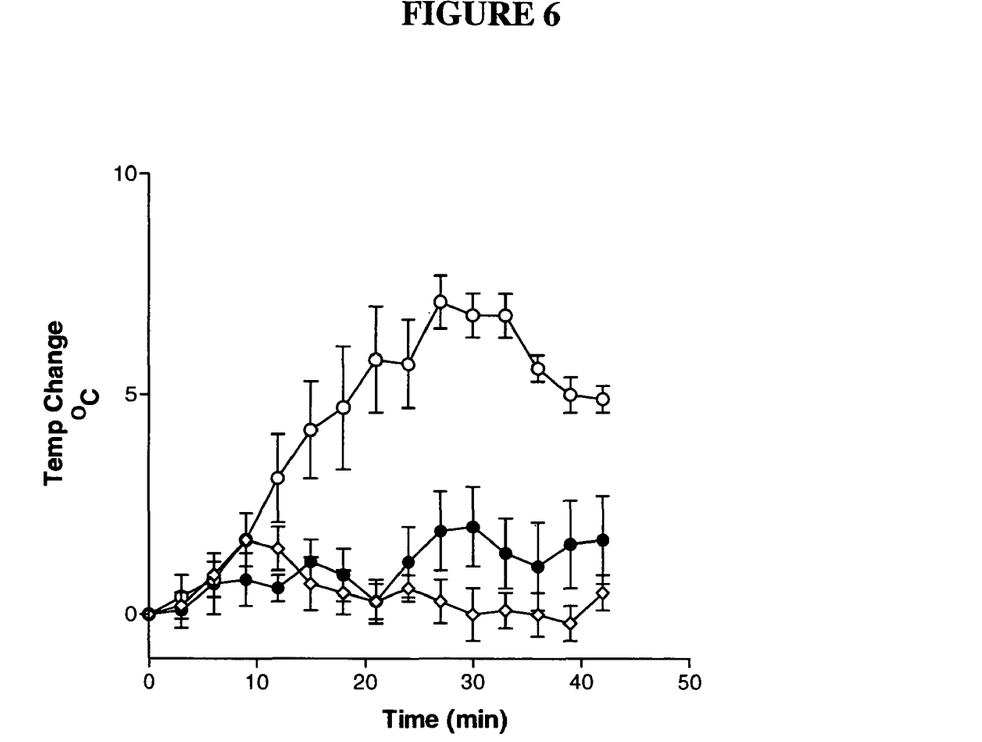
FIG. 6 shows that urantide blocked U-II induced increase in rat ear skin temperature. Rats received either saline, U-II (3 µg/kg), or U-II (3 µg/kg) pre-mixed with 150 µg/kg urantide. Each curve represents the average of 6 animals. U-II (3 µg/kg)—open circle; Urantide (150 µg/kg)—open diamond; and U-II (3 µg/kg) with Urantide (150 µg/kg)-filled circle.

Urantide (at 150 µg/kg) caused no ear flush or ear surface temperature changes of the rat. When urantide (150 µg/kg) was co-administered with U-II (3 µg/kg), the U-II induced ear flush or increase of ear temperature was blocked (FIG. 6), suggesting that U-II mediated ear flush is via the activation of the U-II receptor.

EXAMPLE 3

Involvement of Nitric Oxide and Prostacyclin in the U-II Mediated Ear Flush

The vasodilator response to U-II involves factors from the vascular endothelium, such as nitric oxide and prostacyclin (Bottrill et al, 2000, *Br. J. Pharmnacol.* 130(8): 1865-70; Gray et al., 2001, *Life Sciences* 69(2): 175-180). This example tested the effect of nitric oxide and prostacyclin on the U-II induced increase in the redness or skin temperature of the rat ear. Other factors that are involved in U-II receptor biological activity can be tested using similar protocols.

The nitric oxide syntheses inhibitor, $N^g$ nitro-L-arginine methylester (L-NAME), or prostacyclin inhibitor, indomethacin, was administered to the rat alone or in combination with U-II. L-NAME (N5751, Sigma, 100 mg/kg) suspended in saline was administered to a rat via intraplantar (i.p.) administration 4 hour prior to injecting the rat with the U-II. Indomethacin (17378, Sigma, 30 mg/kg) suspended in carboxymethylcellulose was administered to a rat via p.o. (per os, L—by mouth or orally) 2 hours prior to injecting the rat with the U-II. Dexamethasone (D1756, Sigma, 8 mg/kg) suspended in saline was administered to a rat via i.p. 2 hours prior to injecting the rat with the U-II. After taking a pre-dose or baseline ear surface temperature, 0.1 ml of U-II at various concentrations formulated in sterile normal saline was injection subcutaneously to the mid-scapular region of the rat. The lateral inner ear surface temperature of the rat was measured using a Raytek High Performance Infra-red Thermometer at different time points, wherein the time point of U-II injection was marked as 0 minutes.

Figure 7A:
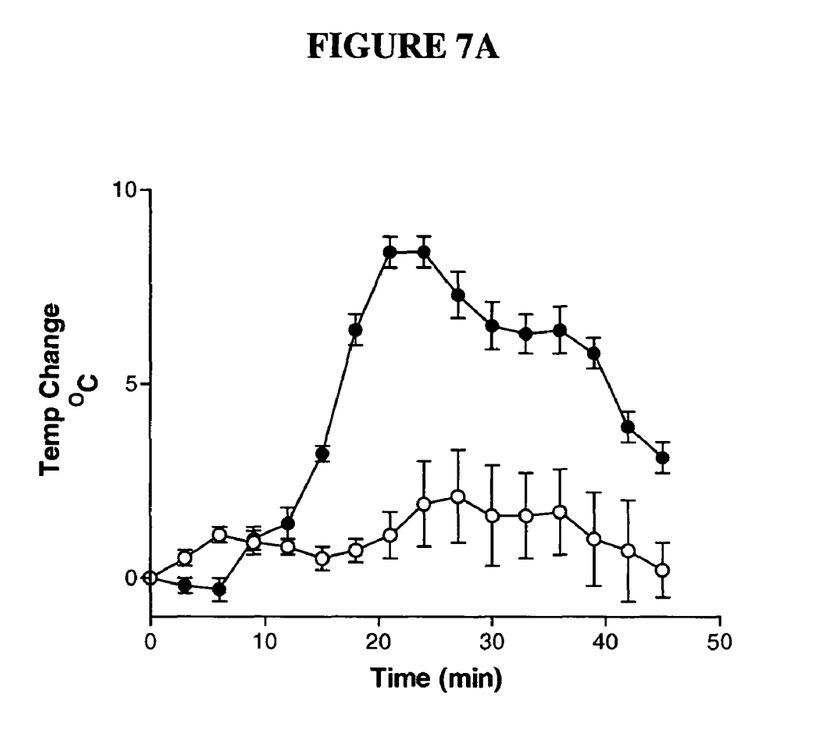
FIG. 7 illustrates that L-NAME and indomethacin each blocked U-II induced increase in rat ear skin temperature. A. Each curve represents the average of 6 animals. U-II (3 µg/kg, s.c.)—filled circle; U-II (3 µg/kg, s.c) and L-NAME (100 mg/kg, i.p.)—open circle. B. Each curve represents the average of 5 animals. U-II (3 µg/kg, s.c.)—filled circle; U-II (3 µg/kg, s.c.) and indomethacin (30 mg/kg, p.o.)—open circle.
Figure 7B:
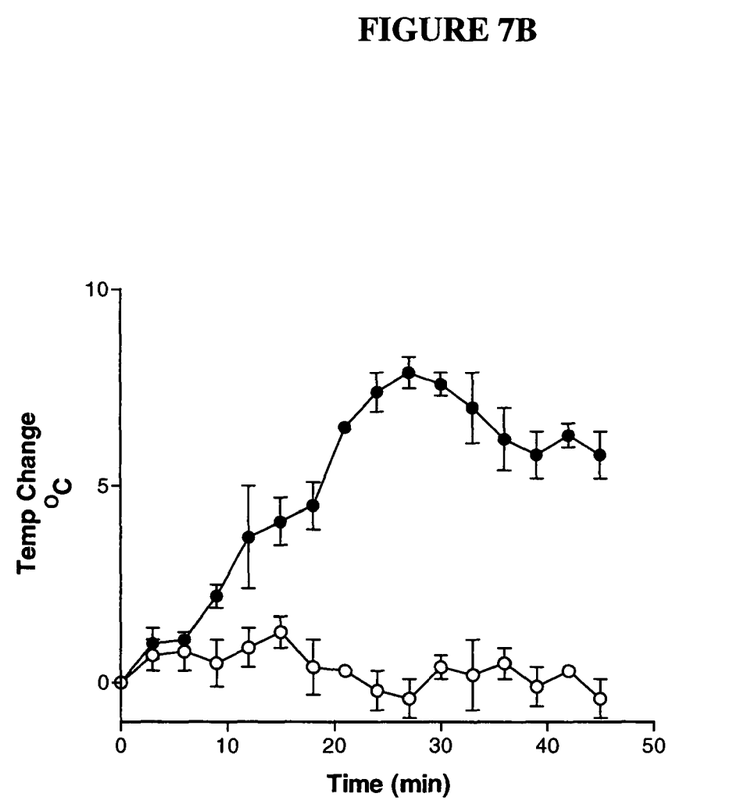

L-NAME alone caused no ear flush or ear surface temperature change of the rat (data not shown). It markedly inhibited the U-II induced ear flush or increase of ear temperature (FIG. 7). Similarly, indomethacin alone caused no ear flush or ear surface temperature change of the rat (data not shown). Indomethacin abolished the U-II induced ear flush or increase of ear temperature (FIG. 7). Dexamethasone, a glucocorticoid analog, caused no ear flush or ear surface temperature change of the rat either when it was administered alone or prior to U-II administration (data not shown).

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of screening a candidate compound for an ability to increase the biological activity of an urotensin II receptor in an animal, comprising the steps of:
   a. administering the candidate compound to the animal;
   b. measuring the redness or the skin temperature of an ear of the animal within an effective time period;
   c. comparing said redness or skin temperature to a baseline redness or skin temperature of the ear or to the redness or skin temperature of the ear prior to administering said candidate compound;
   d. correlating an increase in the redness or the skin temperature of the ear of the animal with the ability of the candidate compound to increase the biological activity of the urotensin II receptor in the animal; and
   e. further testing the candidate compound in an assay for the urotensin II receptor if the administration of the candidate compound results in an increase in the redness of the skin temperature of the ear of the animal.

2. The method of claim 1, wherein the animal is a rat.

3. The method of claim 1, wherein the effective time period is about 5 minutes to about 60 minutes after the administration of the compound to the animal.

4. The method of claim 1, wherein the assay comprises a step of testing the candidate compound for its ability to bind to an urotensin II receptor.

5. The method of claim 1, wherein the assay comprises a step of testing the candidate compound for its ability to elicit an urotensin II receptor mediated change in cell physiology other than the change in the redness or skin temperature of the ear of the animal.

6. The method of claim 5, wherein the cell physiology is selected from the group consisting of total peripheral conductance and cardiac contractility, mean arterial pressure, left ventricular systolic pressure, tachycardia, hypotension, hemodynamic responses and systemic vasodilatation.

7. The method of claim 1, wherein the compound is administered via subcutaneous injection.

8. The method of claim 1, wherein the compound is administered via intramuscular injection.

9. The method of claim 1, wherein the compound is administered via intravenous injection.

10. The method of claim 1, wherein the redness of the ear is measured.

11. The method of claim 1, wherein the skin temperature of the ear is measured.

12. The method of claim 1, wherein both the redness and the skin temperature of the ear are measured.

* * * * *